US006444209B1

(12) United States Patent
Johnson et al.

(10) Patent No.: US 6,444,209 B1
(45) Date of Patent: Sep. 3, 2002

(54) HYBRID BOTULINAL NEUROTOXINS

(75) Inventors: Eric A. Johnson, Madison; Michael C. Goodnough, Stoughton; Marite Bradshaw, Madison; William H. Tepp, Stoughton, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/706,047

(22) Filed: Nov. 3, 2000

Related U.S. Application Data

(63) Continuation-in-part of application No. 09/287,837, filed on Apr. 7, 1999, now abandoned, which is a continuation-in-part of application No. 08/739,477, filed on Oct. 28, 1996, now Pat. No. 5,939,070.

(51) Int. Cl.$^7$ ..................... A61K 39/385; A61K 39/08; C12N 9/52
(52) U.S. Cl. ................. 424/194.1; 424/194.1; 424/239.1; 435/220; 435/842; 435/69.1; 435/69.7; 514/12; 530/350; 530/402; 530/412; 530/825; 536/23.2; 536/23.7
(58) Field of Search ........................... 424/194.1, 239.1; 435/69.1, 69.7, 220, 842; 514/12; 530/350, 402, 412, 825; 536/23.2, 23.7

(56) References Cited

U.S. PATENT DOCUMENTS 5,562,907 A 10/1996 Arnon ..................... 424/236.1

FOREIGN PATENT DOCUMENTS

WO 95/32738 12/1995 .......... A61K/47/48

OTHER PUBLICATIONS

V. Ghetie and E. Vitetta, "Immunotoxins in the Therapy of Cancer: From Bench to Clinic," *Pharmac. Ther.* 63:209–234, 1994.
Hambleton, et al., "Antitoxins and Botulinum Toxin Treatment," *Brit. Med. J.* 304:954–960, 1992.
J. Jankovic and M. Hallett, *Therapy with Botulinum Toxin*, Marcel Dekker, Inc., New York, NY, 1994.
Ludlow, et al., "Therapeutic Use of Type F Botulinum Toxin," *New Eng. J. Med.* 326(5):349–350, 1992.
Montecucco, et al., "Structure and Function of Tetanus and Botulinum Neurotoxins," *Quarterly Review of Biophysics* 28 (4) : 423–472, 1995.
P. Moore, *Handbook of Botulinum Toxin Treatment*, Blackwell Science Inc., Osney Mean, Oxford, UK, 1995.
Peeters, et al., "Comparsion of Four Bifunctional Reagents for Coupling Peptides to Proteins and the Effect of the Three Moieties on the Immunogenicity of the Conjugates," *J. Immun. Meth.* 120:133–143, 1989.
Poulain, et al., "Neurotransmitter Release is Blocked Intracellularly by Botulinum Neurotoxin, and this Requires Uptake of Both Toxin Polypeptides by a Process Mediated by the Larger Chain," *Proc. Natl. Acad. Sci. USA* 85:4090–4094, 1988.
Schantz, et al., "Properties and Use of Botulinum Toxin and Other Microbial Neurotoxins in Medicine," pp. 80–99, 1992.
Schiavo, et al., "An Intact Interchain Disulfide Bond is Required for the Neurotoxicity of Tetanus Toxin," *Infection & Immunology* 58:4136–4141, 1990.
Stecher, et al., "The Light Chain but not the Heavy Chain of Botulinum A Toxin Inhibits Exocytosis from Permeabilized Adrenal Chromaffin Cells," *Federation of European Biochemical Societies* 255(2):391–394, 1989.
Weller, et al., "Cooperative Action of the Light Chain of Tetanus Toxin and the Heavy Chain of Botulinum Toxin Type A on the Transmitter Release of Mammalian Motor End Plates," *Neuroscience Let.* 122:132–134, 1991.

*Primary Examiner*—Karen Cochrane Carlson
*Assistant Examiner*—Chih-Min Kam
(74) *Attorney, Agent, or Firm*—Quarles & Brady LLP

(57) ABSTRACT

A hybrid botulinal neurotoxin is disclosed. In one embodiment, the neurotoxin comprises a combination of a botulinal neurotoxin heavy chain and light chain, wherein the light chain and heavy chain are not of the same serotype and wherein the heavy and light chains are linked by a homobifunctional sulfydryl linker. A method for creating hybrid neurotoxins comprised of different functional domains is also disclosed.

5 Claims, 6 Drawing Sheets

BMH
BISMALCIMIDOHEXANE
SPACER ARM LENGTH 16.1 ANGSTROMS

DPDPB
1,4-DI-[(3',2'-PYRIDYLDITHIO-(PROPIONAMIDO)BUTANE]
SPACER ARM LENGTH 19.9 ANGSTROMS

HYBRID BOTULINAL NEUROTOXINS

CROSS-REFERENCE TO RELATED APPLICATION

The application is a continuation-in-part of Ser. No. 09/287,837 filed Apr. 7, 1999, abandoned, which is a continuation-in-part of Ser. No. 08/739,477 filed Oct. 28,1996, now U.S. Pat. No. 5,939,070.

STATEMENT REGARDING FEDERALLY SPONSORED RESEARCH OR DEVELOPMENT

Not applicable.

BACKGROUND OF THE INVENTION

C. botulinum Toxin Complex

Toxins of the different C. botulinum serotypes are produced in culture as aggregates of neurotoxin and other non-toxic proteins non-covalently associated into a polypeptide complex (Schantz, E., Purification and characterization of C. botulinum toxins, In K. Lewis and K. Cassel, Jr. (eds.), Botulism. Proceedings of a symposium. U.S. Department of Health, Education, and Welfare, Public Health Service, Cincinnati, pp. 91–104, 1964; Sugii, S. and Sakaguchi, G., Infect. Immun. 12:1262–1270, 1975; Kozaki, S., et al., Jpn. J. Med. Sci. Biol. 28:70–72, 1974; Miyazaki, S., et al., Infect. Immun. 17:395–401, 1977; Kitamura, M., et al., J. Bacteriol. 98:1173–1178, 1969; Ohishi and Sakaguchi, Apl. Environ. Microbiol. 28:923–928, 1974; Yang, K. and Sugiyama, H., Apl. Microbiol. 29:598–603, 1975; Nukina, M., et al., Zbl. Bakt. Hyg. 268:220, 1987). Toxin complexes are described as M for medium, L for large and LL for very large. These toxin complexes vary in size from ca. 900 kD for type A LL toxin complex to ca. 300 kD for the type B M complex and type E complex, to 235 kD for type F M complex (Ohishi, I. and Sakaguchi, G., supra, 1974; Kozaki, S., et al., supra, 1974; Kitamura, M., et al., supra, 1969). According to Sugii and Sakaguchi (J. Food Safety 1:53–65, 1977), during culture the proportion of one toxin complex versus another is dependent on the growth medium and conditions. A type B culture grown in the presence of 1 mM $Fe^{+2}$ produces an equal proportion of L and M complexes while the same culture grown in the presence of 10 mM $Fe^{+2}$ produces predominantly M complex.

TABLE 1

Molecular sizes of various C. botulinum toxin complexes.

| Toxin type | Sedimentation coefficient | ca. $M_r$ (kDa) |
|---|---|---|
| LL A | 19S | 900 |
| L A, B, D, G | 16S | 450–500 |
| M A, B, $C_1$, D, E, F, G | 10–12S | 235–350 |

Some of the non-toxic proteins associated with the various toxin complexes have hemagglutinating abilities (Sugiyama, H., Microbiol. Rev. 44:419–448, 1980; Somers, E. and DasGupta, B., J. Protein Chem. 10:415–425, 1991). In particular, non-neurotoxic fractions of the L complexes of type A, B, C, and D have been shown to have hemagglutinating activity. Hemagglutinin fractions isolated from the different serotypes show some serological cross-reactivity. Non-toxic fractions from type A and B serotypes cross-react (Goodnough, M. and Johnson, E., Appl. Environ. Microbiol. 59:2339–2342, 1993) as do non-toxic fractions from types E and F. The nontoxic fractions of types $C_1$ and D are antigenically identical as determined byOuchterlony diffusion (Sakaguchi, G., et al., Jpn. J. Med. Sci. Biol. 27:161–170, 1974).

The non-toxic complexing proteins have been demonstrated to be essential for stabilization of the toxin during passage through the digestive tract (Ohishi and Sakaguchi, supra, 1974; Sakaguchi, G., et al., Purification and oral toxicities of Clostridium botulinum progenitor toxins, In Biomedical aspects of botulism, G. Lewis (ed.), Academic Press, Inc., New York, pp. 21–34, 1981). Pure neurotoxin has a peroral $LD_{50}$ about 100–10,000 times lower than that of toxin complex on a weight basis (Ohishi, I., Infect. Immun. 43:487–490, 1984; Sakaguchi, G., Pharmacol. Therap. 19:165–194, 1983). Presumably, the complexing proteins protect the very labile toxin molecule from proteolytic cleavage and other types of inactivation by enzymes present in the gut and circulatory systems since the toxin and the complexing proteins are very stable in low pH environments.

Analysis by SDS-PAGE has shown that type A toxin complex consists of seven different nontoxic proteins ranging in size from ca. 17 kD to 118 kD in association with a neurotoxic protein of ca. 147 kD (Goodnough, M. and Johnson, E., supra, 1993; Gimenez, J. and DasGupta, B., J. Protein Chem. 12:349–361, 1993; DasGupta, Canad. J. Microbiol. 26:992–997, 1980).

Isolated type A toxin complex has a specific toxicity of $2-3\times10^7$ intraperitoneal $LD_{50}$/mg in 18–22 g white mice. Specific toxicities of other C. botulinum toxin complexes are type B M complex- $4-5\times10^7$ LD50/mg, type C, M complex- $1-2\times10^7$ $LD_{50}$/mg, type D M complex- $7-8\times10^7$ $LD_{50}$/mg, type E M complex- $1\times10^7$ $LD_{50}$/mg, type F M complex- $2-3\times10^7$ $LD_{50}$/mg (Sugiyama, H., supra, 1980), and $8-9\times 10^6$/mg for type G complex (Schiavo, G., et al., J. Biol. Chem. 269:20213–20216, 1994).

C. botulinum Neurotoxin.

The biologically active neurotoxin of C. botulinum is a dichain molecule of ca. 150 kD in molecular weight. The molecule is composed of two 10 fragments or chains that are termed the heavy chain (Hc, ca. 100 kD) and the light chain (Lc, ca. 50 kD) that are covalently connected by one disulfide bond (FIG. 1). The neurotoxin is synthesized by the organism as a single polypeptide called the protoxin and undergoes post-translational processing termed nicking to generate the two separate chains by at least one protease (Yokosawa, N., et al., J. Gen. Microbiol. 132:1981–1988, 1986; Krysinski, E. and Sugiyama, H., Appl. Environ. Microbiol. 41:675–678, 1981). The two chains are covalently bound through a disulfide bridge. The nicking event occurs in the culture fluid for proteolytic C. botulinum and through the activity of an exogenous enzyme such as trypsin in non-proteolytic strains (Yokosawa, N., et al., supra, 1986; DasGupta, B., J. Physiol. (Paris) 84:220–228, 1990; Kozaki, S., et al., FEMS Microbiol. Lett. 27:149–154, 1985).

Functional Domains of Botulinal Neurotoxin.

Binding to cell surface. The carboxyl terminus of botulinal heavy chain is responsible for receptor binding on the cell surface. Initial work done using tetanus toxin, which is very similar in structure to botulinum neurotoxin, showed binding to cell receptors involved a multiple step binding sequence. The ten C-terminal amino acids are essential for initial receptor recognition on the motor neuron via a low affinity binding site while a sequence in the middle of the heavy chain was responsible for higher affinity secondary binding through a different protein receptor (Halpern, J. and Loftus, A., *J. Biol. Chem.* 268:11188–11192, 1993).

Evidence shows that binding by type B botulinum neurotoxin occurs in a similar fashion (Nishiki, T., et al., *J. Biol. Chem.* 269:10498–10503, 1994).

The binding of type B neurotoxin to synaptosomes has been shown to be related to the presence of sialic acid containing motor neuron membrane components such as gangliosides $G_{D1a}$ and $G_{T1b}$ as well as a partially purified 58 kD protein that has been tentatively determined to be synaptogamin. There is minimal binding of the neurotoxin to the 58 kD high affinity receptor in the absence of the low affinity gangliosides. This indicates that the initial low affinity binding to gangliosides which are prevalent on the cell surface by the carboxyl-terminal amino acids is followed by a high affinity binding to the 58 kD protein by an undetermined region that is more amino terminal possibly in the central portion of the heavy chain. Treatment of synaptosomes with proteases and or sialidase decreased binding of the neurotoxin to the synaptosomes.

Channel formation. Once the neurotoxin is bound to the motor neuron via the C-terminus end of the heavy chain, the light chain and the N-terminus of the heavy chain are endocytosed. The proteolytically active light chain is then released into the cytosol of the cell via a translocation event through the phospholipid vesicle membrane. This translocation event is driven by a sequence of amino acids contained in the N-terminal portion of the heavy chain. The predicted sequence responsible for translocation of botulinum toxin type A is from amino acids 650–681 and shows strong sequence homology to tetanus toxin amino acids 659–690 (Montal, M., et al., *FEBS. Lett.* 313:12–18, 1992). Both of these regions contain a high number of hydrophobic amino acid residues which presumably facilitate intercalation into lipid bilayers.

Under the acidic conditions of the vesicle, channels form in the lipid bilayer due to the N-terminal portion of the heavy chain associating into a bundle of amphipathic alpha-helices. These bundles contain four heavy chain portions that allow the light chain to enter the cytosol as evidenced by conformational energy calculations and direct visualization (Montal, M., et al., supra, 1992; Schmid, M., et al., *Nature* 364:827–830, 1993). There are believed to be two different conformations of the channel which may begin forming soon after binding of the C-terminal portion of the heavy chain. One conformation is a low conducting version while the second has a much greater conductance in electrochemical studies (Donovan, J. and Middlebrook, J., *Biochem.* 25:2872–2876, 1986). The difference in the two conformations can be explained by the fact that there is a change in pH from the physiologic condition under which the toxin initially binds and conductance is low to the lower pH values of the endocytotic vesicle where conductance is higher. The rate of conductance through channels has been shown to be highest at a pH of about 6.1 and lower at pH values closer to neutral (Donovan, J. and Middlebrook, J., supra, 1986).

Enzymatic activity in neuron/specificity for substrate. In order to describe the mechanism of botulinum neurotoxins in general, the synaptic vesicle docking cascade must be understood for it is the inhibition of the release of the neurotransmitter acetylcholine from cholinergic motor neurons which leads to the classic flaccid paralysis seen in botulinum intoxicated muscle tissue.

The key event in the release of neurotransmitter is exocytosis of the synaptic vesicle contents through fusion of the synaptic vesicles with the phospholipid plasma membrane. Normally, synaptic vesicles are pre-docked on the inside of the plasma membrane through a series of docking proteins and acetylcholine molecules are exocytotically released by an increase in the intracellular $Ca^{+2}$ concentration (Sudhof, T., *Nature* 375:645–653, 1995). The docking proteins and their relationship to the synaptic vesicles is shown in FIG. 2.

The neurotoxic activity of all seven serotypes of neurotoxin is related to the fact that the light chains of botulinum toxin as well as the light chain of tetanus toxin are known to be zinc endopeptidases. The zinc binding region of the light chain of the neurotoxins is highly conserved and is very homologous between the serotypes. It includes a region that possesses the zinc binding motif HExxH surrounded by sequences that show a lesser degree of homology. The intracellular target for each serotype is one or more of the proteins involved in docking of the acetylcholine containing vesicles to the neuronal membrane. Cleavage of the various neurotoxin substrates inhibits the docking of the vesicles with the plasma membrane and, hence, the release of the neurotransmitter into the synaptic junction. The various substrates for the seven serotypes of botulinum neurotoxin as well as tetanus toxin are shown in Table 2.

TABLE 2

Intracellular substrates of clostridial neurotoxins (adapted from Oguma K. et al., *Microbiol. Immunol.* 39:161–168, 1995).

| Neurotoxin serotype | Intracellular target | Cleavage site |
| --- | --- | --- |
| A | SNAP-25 | Gln 197-Arg 198 |
| B | Synaptobrevin-2 (VAMP-2) | Glu 76-Phe 77 |
| $C_1$ | Syntaxin | near C-terminus |
| D | Synaptobrevin-1 (VAMP-1) | Lys 61-Leu 62 |
|   | Synaptobrevin-2 (VAMP-2) | Lys 59-Leu 60 |
| E | SNAP-25 | Arg 180-Ile 181 |
| F | Synaptobrevin-1 (VAMP-1) | Gln 60-Lys 61 |
|   | Synaptobrevin-2 (VAMP-2) | Gln 58-Lys 59 |
| G | Synaptobrevin-1 (VAMP-1) | Ala 83-Ala 84 |
|   | Synaptobrevin-2 (VAMP-2) | Ala 81-Ala 82 |
| Tetanus toxin | Synaptobrevin-2 | Glu 76-Phe 77 |

Because patients have developed immunity to treatment with type A botulinal toxin (Borodic, G., et al., *Neurology* 46:26–29, 1996), a toxin preparation that avoids that immunological problem is highly desired.

SUMMARY OF THE INVENTION

In one embodiment, the present invention is a hybrid botulinal neurotoxin comprising heavy and light chain combinations that are not present in nature. In a preferred embodiment, the present invention is a hybrid botulinal neurotoxin comprising heavy and light chains that are isolated from botulinal neurotoxin molecules that are not of the same serotype, wherein the chains are connected by a reducible homobifunctional sulfhydryl linker. In an especially preferred embodiment, the hybrid botulinal neurotoxin comprises a combination of functional domains from different botulinal toxin serotypes.

The present invention is also a method for creating hybrid botulinal neurotoxin comprising the steps of isolating botulinal neurotoxin heavy and light chains from different serotypes and combining the heavy and light chains into a hybrid neurotoxin. In one embodiment of this method, the heavy or light chain is produced from a recombinant gene construct and the isolation is from a recombinant microorganism. In another embodiment, the heavy and light chain are isolated molecules from either native or recombinant organism and combined together natively by a homobifunctional linker between heavy and light chain.

In a separate embodiment of the method, hybrid genes contain the translocation domain of the heavy chain from one serotype, receptor binding domain of the heavy chain from another serotype, combined with the light chain of a third C. botulinum serotype. Thus, it is possible to construct a variety of new toxin molecules by combining any of the three functional domains from any C. botulinum neurotoxin serotypes.

It is an object of the present invention to create a hybrid botulinal neurotoxin.

It is another object of the present invention to create a hybrid botulinal neurotoxin by recombinant gene constructs encoding botulinal neurotoxin heavy and light chains.

It is another object of the present invention to combine botulinal neurotoxin heavy and light chains isolated from both native and recombinant a sources.

It is another object of the present invention to combine regions of the genes within the three functional domains of the botulinal neurotoxins to make novel hybrid toxins.

Other objects, features and advantages of the present invention will become obvious after examination of the specification, claims and drawings.

BRIEF DESCRIPTION OF THE DRAWING

FIG. 1 is a schematic diagram of the activation of C. botulinum neurotoxin by formation of separate heavy and light chains covalently linked by a disulfide bond.

FIG. 2 is a schematic diagram of the iodoacetamide modifications of free thiols in type A neurotoxin.

DESCRIPTION OF THE INVENTION

1. In General

Figure 3:
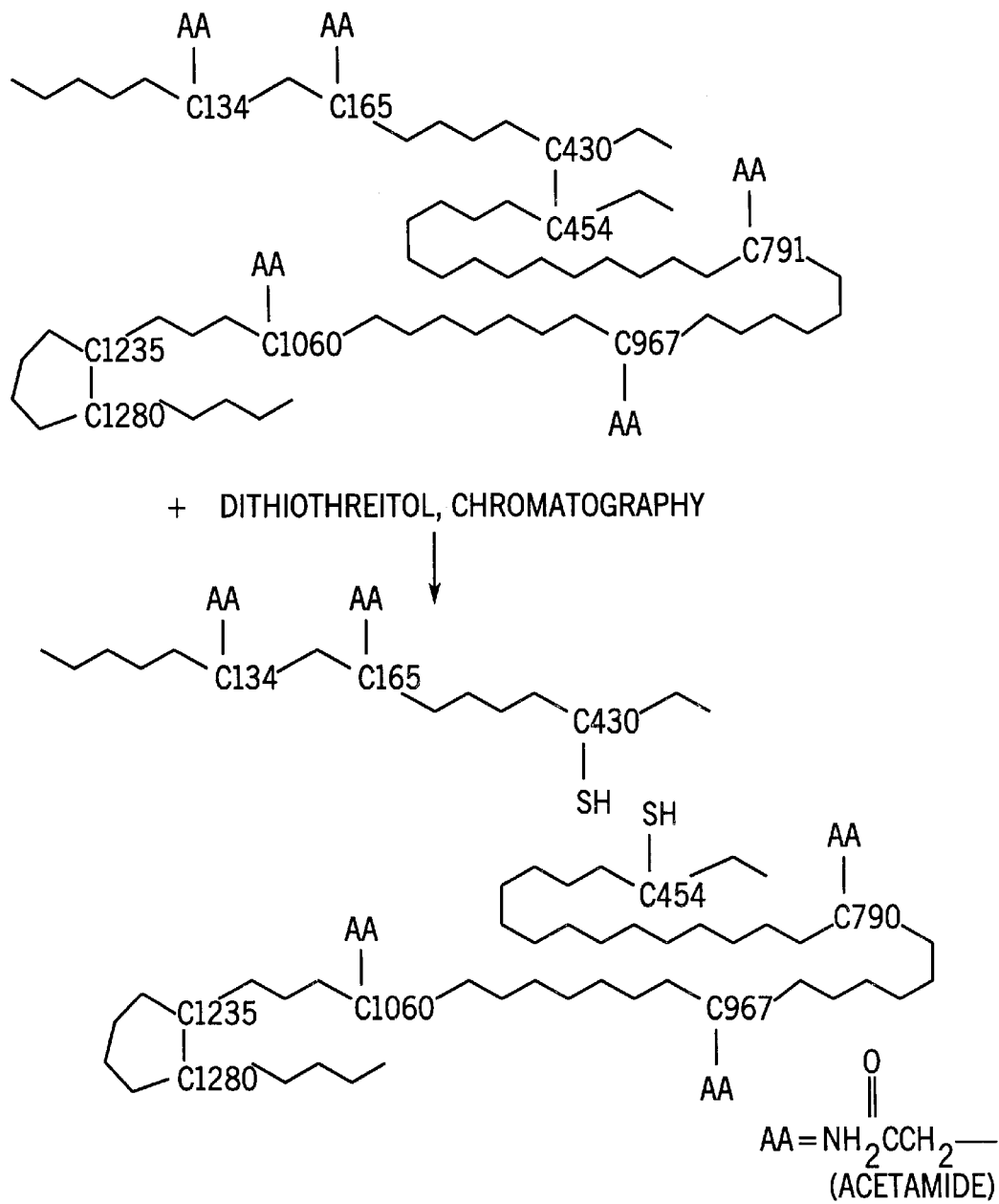
FIG. 3 is a schematic diagram of the separation of sulfhydryl modified type A neurotoxin heavy and light chains.

The present invention is hybrid botulinal neurotoxin comprising a heavy and light chain wherein the heavy chain and light chain are not natively connected. By not "natively connected" we mean that the hybrid toxin molecule contains components that are not found together in their natural form.

In one preferred form, the present invention is a heavy chain isolated from a botulinal neurotoxin of a first serotype and a light chain isolated from a at botulinal neurotoxin of a second serotype. In another embodiment, the present invention is a heavy and light chain encoded on a recombinant gene construct and expressed in a recombinant microorganism. This recombinant version of a hybrid botulinal toxin may contain either heavy or light chain with recombined functional domains.

Figure 1:
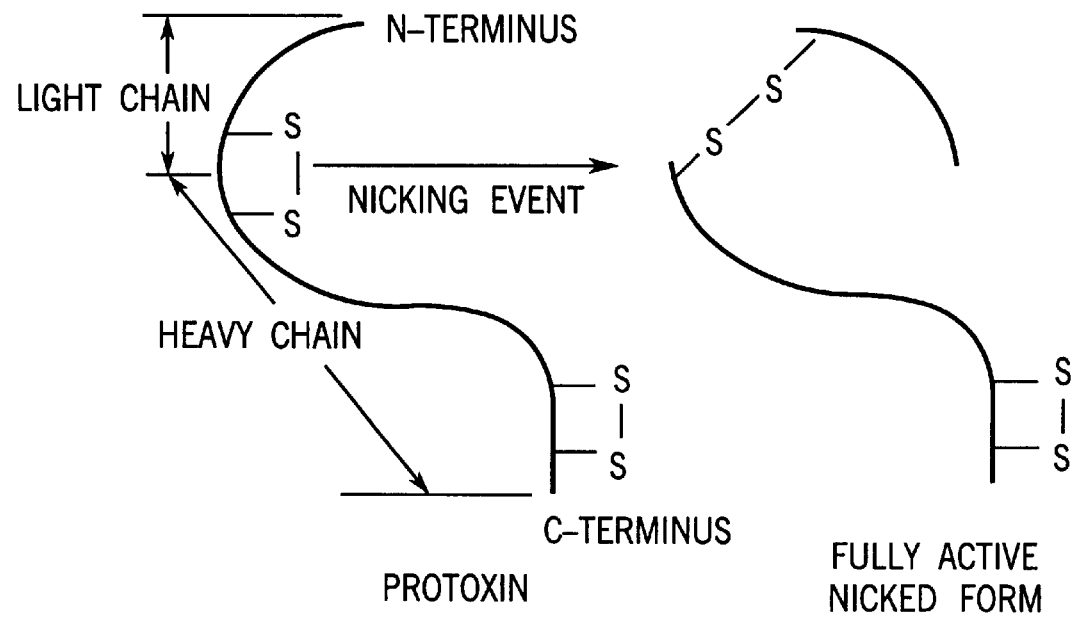

The group of seven serologically distinct botulinal neurotoxins produced by Clostridium botulinum is characterized by having a very specific target in humans as well as having an extremely high specific toxicity. The target of botulinal neurotoxins is the pre-synaptic junctions of motor neurons. All seven serotypes of toxin cause a flaccid paralysis due to the inhibition of the release of the neurotransmitter acetylcholine. The seven serotypes are further characterized by having distinctly different intracellular substrates all of which are involved in the docking of synaptic vesicles containing acetylcholine (Schiavo, G., et al., J. Biol. Chem. 268:11516–11519, 1993a; Schiavo, G., et al., J. Biol. Chem. 268:2378–23787, 1993b). The dichain toxin molecules consist of a binding and internalization portion which is located within the heavy chain along with a catalytic zinc endopeptidase which is located within the light chain. These two portions are covalently connected by a disulfide bond (FIG. 1).

The neurotoxin is typically produced in culture as part of a non-covalently bound complex of proteins, some of which have hemagglutinating ability. Molecular weights of these toxin complexes varies from 235 kDa for type F to 900 kDa for type A. The duration of action of paralysis of the individual toxin serotypes varies with types A the longest duration of action and B and F being considerably less. The type A botulinum toxin (Botox™) product currently licensed by the U.S. Food and Drug Administration for treatment of involuntary muscle disorders consists of lyophilized type A toxin complex. The solely approved batch of toxin was produced at the University of Wisconsin-Madison Food Research Institute in 1979.

The prevalence of patients developing immunity to treatment with type A botulinal toxin (Botox®, Allergan, Inc., Irvine, Calif.) has been documented (Borodic, G., et al., supra, 1995; Borodic, G., et al., supra, 1996). In patients showing immunity, the use of botulinal toxin gives none or only minimal relief from the affliction they are being treated for due to neutralization of the toxin by circulating antibodies or other mechanisms of immunity.

In an effort to avoid antibodies specific for type A toxin while still providing relief from the myogenic disorders for which patients are being treated, we have synthesized hybrid toxin molecules that, in one embodiment, consist of the targeting and internalization portion (heavy chain) of one toxin serotype and the catalytic portion of a different serotype (light chain). This approach gives the inherent binding specificity of botulinal heavy chain from the first serotype and the potent catalytic capability of the light chain from the second serotype.

2. Creation of Hybrid Toxins By Combination of Botulinal Toxin Subunits or Domains In one embodiment of the invention, the hybrid neurotoxins are constructed by purifying the individual heavy and light chains from native sources according to published methodologies (Sathyamoorthy, V. and DasGupta, B., J. Biol. Chem. 260:10461–10466, 1985). Work in our laboratory has shown that when the individual heavy and light chains are recombined they do not spontaneously reform intact neurotoxin molecules, although the toxicity of such preparations approaches that of native toxin in some model systems.

A linker has been used between the two chains in order to effectively regenerate covalently linked toxin molecules.

Figure 5:
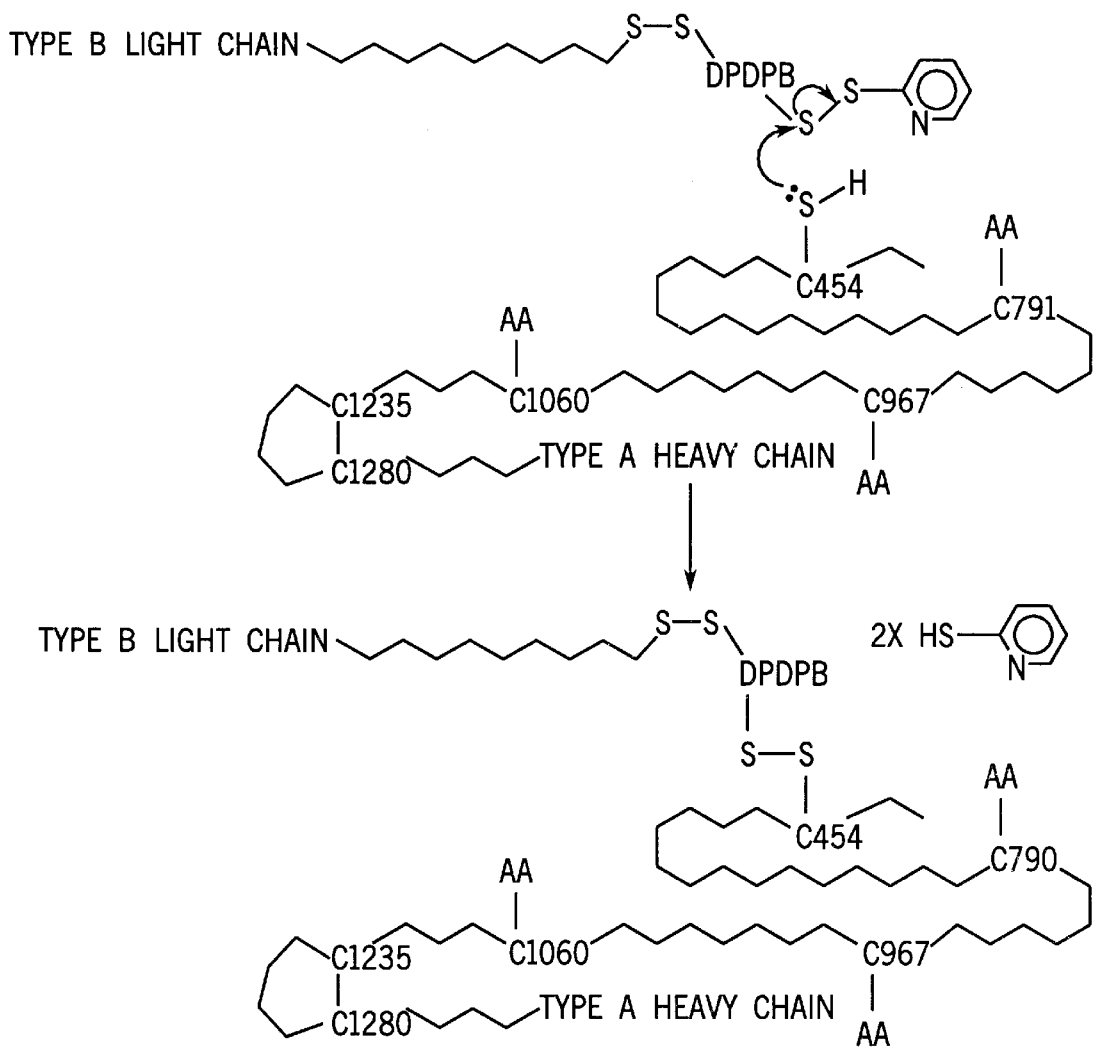
FIG. 5 is a schematic diagram of the conjugation of sulfhydryl modified type B light chain and type A heavy chain via homobifunctional linker DPDPB.

Therefore, the individual heavy and light chains will typically be recombined by adding a linker, such as succinimidyl-3-(2-pyridyldithio)propionate (SPDP) or 1,4-di[3',2'-pyridyldithio-(propionamido) butane] (DPBPB), to either the heavy chain followed by addition of the reduced light chain or to the light chain followed by addition of reduced heavy chain. Particularly preferred reducible homobiofunctional linkers are described below and include those in FIG. 5 (DPDPB) and FIG. 6 (DTME). By "reducible" we mean linkers which contain one or more disulfide bonds. These disulfide-bond-containing linkers typically are reactive with free sulfhydryls via 2-pyridylthio groups in the case of DPDPB or maleimide groups in the case of DTME. This manipulation results in a covalently linked dichain molecule having the individual chains connected by a disulfide linkage similar to the native dichain molecule.

For example, in the Examples below we describe a hybrid which consists of the purified heavy chain of serotype B neurotoxin and the catalytic light chain of type A neurotoxin. This combination gives the following advantages: (1) The hybrid has the duration of action of the original type A toxin; (2) the hybrid has ⅓ (or less) the type A specific antigenicity which may allow it to be used to treat patients that are resistant to native type A toxin; and (3) in combination with type A toxin, a hybrid consisting of type A heavy chain and the light chain of type B may give even longer duration of action than type A alone due to the fact that the two different light chains (A and B) have different intracellular targets and thus may exhibit a synergistic affect.

Preferable combinations include A and C light chains for duration of action and B, E, D, F, and G heavy chains for different antigenicity.

Figure 4:
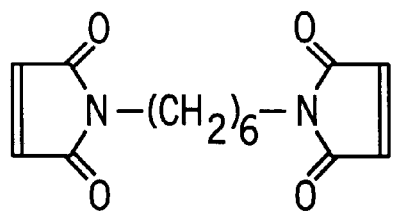
FIG. 4 is a diagram of preferred homobifunctional linker structures.
Figure 4:
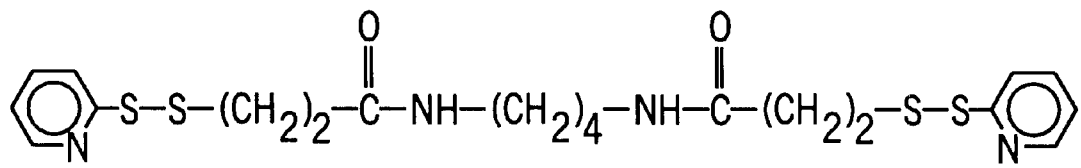

The heavy and light chains may also be recombined by adding a homobifunctional linker, such as described below and in FIG. 4.

Figure 2:
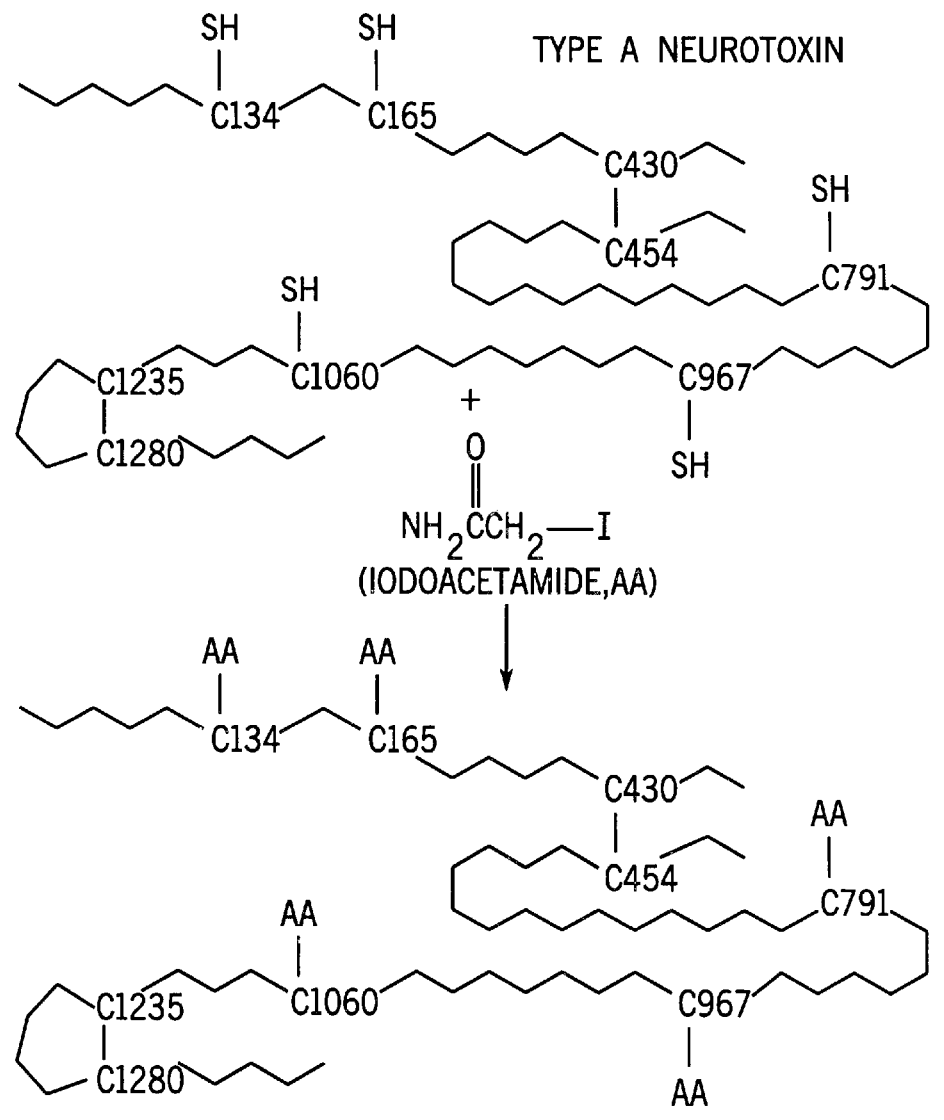

Preferably, one would first block free sulfhydryls that would interfere with subsequent biochemical reactions. The Examples below describe this procedure by the method of Schiavo, et al., *Infect. Immun.* 58:4136–4141, 1990. Modification of type A neurotoxin prior to chain separation is also illustrated in FIG. 2. One would modify both chains in a similar fashion.

Preferably, one would also separate the heavy and light chains as described schematically in FIG. 3 and in the Examples below.

3. Creation of Hybrid Toxins by Recombinant Methods

In another embodiment, the hybrid neurotoxins are constructed by genetic recombination of the neurotoxin gene sequences. For example, one would join the coding sequence for the entire heavy chain of serotype B neurotoxin (or parts of the chain) and the light chain of type A neurotoxin in a recombinant gene construct and express this coding sequence as a hybrid toxin. Alternatively, one might express the two neurotoxin chains individually, isolate the separate neurotoxin chains as expressed proteins and combine the chains with a linker, as described above for the protein work.

In one embodiment, one may manipulate the neurotoxin gene sequences to combine functional domains from different serotypes in a novel gene. For example, the gene segment coding the catalytic light chain of a type A neurotoxin, the gene segment coding the channel forming domain of a type B neurotoxin and the gene segment coding the receptor-binding domain of a type E neurotoxin may be joined together by genetic engineering techniques, and hybrid neurotoxin expressed in the recombinant microorganism.

EXAMPLES

Isolation of Native Toxin Light and Heavy Chains and Formation of Hybrid Toxin

1. Materials and Methods

Bacterial strains and culture production. The Hall A strain of type A *C. botulinum* was used to produce type A complex. This strain was originally obtained from Dr. J. H. Mueller at Harvard University and was further screened for high toxin titers at Fort Detrick, MD and at the University of Wisconsin, by Dr. E. J. Schantz, E. A. Johnson and coworkers. This strain is routinely used for production of type A botulinum toxin due to high toxin titers and the rapid onset of cell lysis (usually within 48 hours). Type B toxin was produced from the proteolytic Okra B strain of *C. botulinum*. This strain was obtained from the Food Research Institute culture collection. Other serotypes of *C. botulinum* are stored in the University of Wisconsin Food Research Institute Culture Collection.

Stock cultures of *C. botulinum* Hall A and Okra B were grown statically in 15 ml Hungate tubes containing 10 ml of cooked meat medium +0.3% dextrose (CMM, Difco Laboratories, Detroit, Mich.) under an anaerobic atmosphere (80% $N_2$, 10% $CO_2$, 10% $H_2$) at 37° C. for 24 hours and frozen at −20° C. until use. CMM cultures of the Hall A strain give toxin titers in excess of $10^6$ $LD_{50}$/ml in 48–72 hours. CMM cultures of the Okra B strain give toxin titers in the range of 5–9×$10^5$ $LD_{50}$/ml in 48–96 hours. Type B toxin titers may be increased by trypsinization to increase the proportion of fully active nicked toxin molecules. However, this procedure would necessitate the removal of trypsin and was not done in this study.

For toxin production, cultures of Hall A and Okra B were grown statically in 12–15 liter volumes of toxin production medium (TPM) consisting of 2.0% casein hydrolysate (Sheffield Laboratories, Norwich, N.Y.), 1.0% yeast extract (Difco), and 0.5% dextrose, pH 7.3–7.4, for 5–7 days at 37° C. Cultures of Hall A and Okra B showed heavy growth in this medium during the first 24–48 hours followed by autolysis of the cultures which was evident as a clearing and settling over the next 48–120 hours. The Okra B strain did not produce toxin titers as high as Hall A nor did it lyse as rapidly or completely.

Type A toxin complex purification. Type A toxin complex was purified chromatographically by the method of Tse, et al. (Tse, C., et al., *Eur. J. Biochem.* 122:493–500, 1982). Extracts of the first acid-precipitated material were dialyzed against 50 mM sodium citrate, pH 5.5, and chromatographed at room temperature on a 1 liter DEAE-Sephadex A-50 column (Sigma Chemical Co., St. Louis, Mo.) equilibrated with the same buffer. One-tenth the column volume or less was chromatographed in a single passage with the toxin complex eluting in the first column volume without a gradient. Fractions from this protein peak which had a 260/278 absorbance ratio of less than 0.6 were pooled and precipitated by the addition of solid ammonium sulfate to ca. 60% saturation (39 g/100 ml). Purified type A toxin complex had a specific toxicity of 3.0–3.2×$10^7$ $LD_{50}$/mg.

Type A neurotoxin purification. Type A neurotoxin was purified from the associated non-toxic proteins of the complex by a modification of the method of Tse, et al. (supra, 1982). Toxin complex recovered from the DEAE-Sephadex A50, pH 5.5 column was precipitated by addition of 39 g of solid ammonium sulfate/100 ml. The precipitated toxin complex was collected by centrifugation (12,000×g, 5–10° C., 20 minutes), dialyzed against 25 mM sodium phosphate, pH 7.9, and applied to a DEAE-Sephadex A50 column equilibrated with the same buffer. Toxin was separated from the non-toxic proteins of the complex and eluted from the column with a linear 0–0.5 M sodium chloride gradient. Toxin eluted in the first peak and fractions which had 260/278 nm absorbance ratios <0.6 were pooled and precipitated by adding 39 g ammonium sulfate/100 ml. Material recovered from the DEAE-Sephadex A50 column at pH 7.9 was further purified by chromatography on SP-Sephadex C50 at pH 7.0. Precipitated toxin from DEAE-Sephadex A50 columns at pH 7.9 was collected by centrifugation (12,000×g, 5–10° C., 20 minutes) and dialyzed against 25 mM sodium phosphate, pH 7.0. The dialyzed toxin was applied to 25 ml SP-Sephadex C50 in 25 mM sodium phosphate, pH 7.0. Contaminating material did not bind to the column under these conditions. The purified neurotoxin was eluted with a linear 0–0.25 M sodium chloride gradient and precipitated by addition of 39 g ammonium sulfate/100 ml. Type A neurotoxin had a specific toxicity of $8.0 \times 10^7$ to $1.0 \times 10^8$ $LD_{50}$/mg and was judged to be >95% pure by SDS-PAGE.

Type B toxin complex purification. Type B toxin complex was purified from crude culture fluid by a method involving the chromatographic procedure of Tse, et al. (supra, 1982). Cultures of C. botulinum Okra B were acid precipitated to pH 3.4 using 3 N sulfuric acid. The precipitate was extracted once by adding $CaCl_2$ to a final concentration of 75 mM and raising the pH to 6.5–6.8 analogous to purification of type A toxin. The clarified extracts were reprecipitated by lowering the pH to 3.7 with 1 N HCl. The second precipitate was then extracted with 50 mM sodium citrate buffer, pH 5.5, and the clarified extract dialyzed against the same buffer. A mixture of L and M type B toxin complexes was isolated by chromatography on 1 liter volumes of DEAESephadex A50 equilibrated with 50 mM sodium citrate, pH 5.5. One-tenth the column volume or less was purified in a single passage with type B toxin complex eluting in the first column volume without a gradient. Fractions which had 260/278 nm absorbance ratios <0.6 were pooled and precipitated by addition of 39 g ammonium sulfate/100 ml. The extinction coefficient used for type B toxin complex was $A_{278}$ 1.85=1 mg/ml (Beers, W. and Reich, E., J. Biol. Chem. 244:4473–4479, 1969). This pool represented type B toxin complex with a specific toxicity of $4.2 \times 10^7$ $LD_{50}$/mg.

Type B neurotoxin purification. Type B neurotoxin was purified from the complex by a method involving the methods of Tse, et al. (supra, 1982) and Moberg and Sugiyama (Moberg, L. and Sugiyama, H., Appl. Environ. Microbiol. 35:878–880, 1978). Type B toxin complex in 25 mM sodium phosphate, pH 7.9, was applied to DEAE Sephadex A50 (Sigma) equilibrated with the same buffer. Partially purified type B neurotoxin was eluted from this column with a 0–0.5 M sodium chloride gradient. Type B toxin fractions which had 260/278 nm absorbance ratios <0.6 were pooled and precipitated by the addition of 39 g ammonium sulfate/100 ml. Precipitated material was dialyzed against 25 mM sodium phosphate, pH 6.3, and applied to a pAPTG-Sepharose 4 B column (p-aminophenyl-6-D-thiogalactopyranoside) equilibrated with the same buffer (Sigma Chemical Co.). The charged column was washed with 5–10 column volumes of the loading buffer and the toxin eluted by changing the buffer system to 100 mM sodium phosphate, 1.0 M sodium chloride, pH 7.9. Fractions which had 260/278 nm absorbance ratios <0.6 were pooled and precipitated by addition of 39 g ammonium sulfate/100 ml. Purified type B neurotoxin had a specific toxicity of $9.0 \times 10^7 - 1.1 \times 10^8$ $LD_{50}$/mg and was judged to be >95% pure by SDS-PAGE.

Type A neurotoxin chain separation. The separate heavy and light chains of type A neurotoxin were purified by the method of Sathyamoorthy and DasGupta (supra, 1985). Briefly, purified type A neurotoxin was dissolved in 20 mM sodium borate, 40 mM sodium phosphate, pH 8.4, and dialyzed against the same overnight. Approximately, 15 mg of the dialyzed neurotoxin was applied to a column of QAE-Sephadex (1.6 cm×10 cm, Pharmacia) equilibrated with the pH 8.4 buffer at 4° C. After washing with 5 column volumes of loading buffer, the column was washed with one-half column volume of loading buffer containing 10 mM dithiothreitol (DTT) as a reducing agent followed by a wash with one-half the column volume of loading buffer containing 100 mM DTT plus 2 M urea. The flow was stopped overnight (16 hours) and resumed the following morning with loading buffer containing 10 mM DTT plus 2 M urea. The light chain eluted at this point. Heavy chain was recovered by elution with loading buffer containing 10 mM DTT, 2 M urea, and 200 mM sodium chloride. Heavy chain thus eluted contained a small portion of unnicked neurotoxin (<2%).

Light chain was further purified by chromatography on SP-Sephadex. Fractions from the QAE column were dialyzed against 20 mM sodium phosphate, 5 mM DTT, pH 5.95 and loaded onto SP-Sephadex (1.6×10 cm) equilibrated with the same buffer at 4° C. After washing with five column volumes of loading buffer, purified light chain was eluted with a linear gradient of 0–0.2 M sodium chloride. Specific toxicities of light chain preparations were $10–100 \times 10^7$ $LD_{50}$/mg of protein and were >95% pure as shown by SDS-PAGE.

Type A heavy chain was further purified by dialyzing fractions from the QAE column against 20 mM sodium phosphate, 5 mM DTT, pH 7.5, followed by chromatography on DEAE-Sephadex (1.6×10 cm) equilibrated with the same buffer. Contaminating light chain was eluted by washing the column with 5–8 column volumes of loading buffer and the heavy chain separated from the residual unnicked neurotoxin with 50 ml of a linear 0–0.12 M sodium chloride gradient followed by a second linear gradient of 150 ml of 0.12–0.6 M sodium chloride. Specific toxicities of heavy chain preparations were 25–200 $LD_{50}$/mg and were judged to be >95% homogeneous.

Type B neurotoxin chain separation. Heavy and light chains of type B neurotoxin were purified in a similar fashion with the following exceptions. Type B neurotoxin was completely nicked by incubating the neurotoxin with 1:40 (w/w) TPCK treated trypsin (Sigma) in 50 mM sodium acetate, pH 6.0, for 30 minutes at 37° C. Soybean trypsin inhibitor (Sigma) was added to a final concentration of 2× the trypsin (w/w) and the mixture dialyzed overnight against 15 mM sodium borate, 30 mM sodium phosphate, pH 8.4. The heavy and light chains were separated on a column of QAE-Sephadex (1.6×10 cm) equilibrated with 15 mM sodium borate, 30 mM sodium phosphate, pH 8.4, according to the method used for type A.

Type B light chain eluted from the QAE column was further purified on SP-Sephadex similarly to type A light chain. The preparation was estimated to be >95% pure by SDS-PAGE and had a specific toxicity of 10–100 $LD_{50}$/mg.

Type B heavy chain which was recovered from the QAE column was separated from the residual unnicked neurotoxin on DEAE-Sephadex similarly to type A heavy chain. The preparation was >95% pure and had a specific toxicity of approximately 100–500 $LD_{50}$/mg.

Electrophoresis and immunoblotting. Protein samples were examined electrophoretically using the Pharmacia Phastsystem (Pharmacia LKB Inc., Piscataway, N.J.) according to the manufacturer's instructions. Precast 12.5% acrylamide gels (Pharmacia) were stained with 0.1% coomassie brilliant blue R250 in 16.7% acetic acid, 41.7% methanol. Gels were destained in 7.5% acetic acid, 25% methanol. Samples for electrophoresis were solubilized in 50 mM Tris-HCl, 5 M urea, 5% SDS, 20% glycerol, pH 6.8. Some samples were reduced by addition of dithiothreitol to a final concentration of 0.5%. All samples for SDS-PAGE were boiled for >5 minutes prior to electrophoresis. Protein bands from SDS-PAGE gels for analysis via immunoblotting were transferred to PVDF membranes using the Pharmacia semi-dry electrotransfer system according to the manufacturers instructions. Serotype specific antibodies used for detection of type A and B toxins and separate chains were produced in rabbits at the Food Research Institute and were conjugated to alkaline phosphatase. The antibodies did not cross-react with the different serotypes. Alkaline phosphatase was detected using Sigma Fast nitro blue tetrazolium/bromo-chloro-indole phosphate tablets according to the manufacturer's instructions (Sigma).

Toxin assays. Toxin titers were estimated in mice using the intravenous method of Boroff and Fleck (Boroff, D.A., and Fleck, U., *J. Bacteriol.* 92:1580–1581, 1966) and the intraperitoneal method of Schantz and Kautter (Schantz, E. and Kautter, D., *J. Assoc. Off. Anal. Chem.* 61:96–99, 1978) in 18–22 g, female, ICR strain mice. Time-to-death values obtained from intravenous titration of type A and B toxin samples were converted to intraperitoneal $LD_{50}$/ml using a standard curve generated in our laboratory with type A complex. Botulinal toxin for titration was dissolved in 50 mM sodium phosphate, pH 6.8, and then further diluted as required in 30 mM sodium phosphate, 0.2% gelatin, pH 6.4.

Linker addition to type B heavy chain. Approximately 3 mg of type B heavy chain eluted from the DEAE-Sephadex column at pH 7.5 was concentrated to approximately 1 mg/ml in a 15 ml Centricon ultra-filtration unit having a molecular weight cut off of 10,000 daltons (Amicon, Beverley Mass.) according to the manufacturer's recommendation. Material which precipitated during the concentration was removed by centrifugation in a refrigerated microfuge (12,000×g) and the heavy chain passed through a Pharmacia PD10 desalting column equilibrated with 100 mM sodium phosphate, pH 8.0, at 4° C. to remove residual DTT. SPDP linker (100 mM in dimethyl sulfoxide) was added to the heavy chain at a 2× molar ratio and allowed to react for 60 minutes at 4° C. Unreacted linker was removed by chromatographing the heavy chain+linker on a second PD10 desalting column equilibrated with 50 mM sodium phosphate, 150 mM sodium chloride, 1 mM EDTA, pH 7.5 (PBSE).

Reduction of type A light chain. Type A light chain eluted from the SP-Sephadex column, pH 5.95, was concentrated to approximately 1 mg/ml using a Centricon in similar fashion to the type B heavy chain. Cysteine residues on the type A light chain were reduced by addition of DTT to a final concentration of 50 mM and incubated on ice for 30 minutes. The DTT was then removed by gel-filtration on a PD1 0 column equilibrated with PBSE at 4° C.

Conjugation of type B heavy chain plus linker to reduced type A light chain. The above two procedures were run as close to simultaneously as possible such that the two preparations could be combined as quickly as practical in order to reduce the amount of homologous dimerization (i.e. heavy chain-heavy chain or light chain-light chain). The conjugation was allowed to proceed for two hours at 4° C. at which time the reaction was stopped by addition of ammonium sulfate to 60% saturation.

2. Results

The conjugate was analyzed by SDS-PAGE using Coomassie blue staining for total protein and by immunostaining of electrotransferred SDS-PAGE gels for detection of the different chains. Staining of unreduced samples for total protein revealed bands of 200, 150, 100, and 50 kD. The 200 kD band was shown by immunoblot to be a dimer of the type B heavy chain while the 100 kD band was mainly type B heavy chain in the monomeric form. There was slight reaction of the 100 kD band with type A specific antibodies when the samples were unreduced indicating that the type A light chain had also dimerized to a small degree. The 150 kD band reacted strongly with type B specific antibodies as well as type A specific antibodies indicating that the conjugation was successful. The 50 kD band was unreacted type A light chain in the monomeric form. Samples that were reduced by addition of DTT showed bands of 100 kD and 50 kD which represented the starting components, namely, type B heavy chain and type A light chain.

The conjugate had an intraperitoneal specific toxicity in mice of approximately $10^6$ $LD_{50}$/mg of protein which was >1,000 fold the toxicity of the starting materials.

3. Discussion

Advantages of hybrid. The advantages of the botulinal toxin hybrids that can be generated using any of the purified heavy and light chains are: (1) the duration of action of the hybrid is dependent on the serotype of the light chain that is used; for instance a hybrid consisting of type B heavy chain and type A light chain should have the duration of action of type A neurotoxin, and (2) the type A specific immunogenicity of the B heavy chain-A light chain conjugate should be less than one-third that of type A neurotoxin because the molecule has a third of the amino acid sequence of native type A neurotoxin but the light chain of type A neurotoxin is less immunogenic than the heavy chain (Goodnough and Johnson, unpublished results). Therefore, it may be possible to use conjugates that contain the light chain of type A neurotoxin to treat dystonias in patients that are showing immunity to type A neurotoxin because a majority of the antibodies the patient produces are directed toward the heavy chain of the native type A neurotoxin.

Additionally, conjugates may act synergistically with different serotypes of native neurotoxin or different conjugates due to the fact that the various serotypes have different intracellular targets within the motor neuron.

4. Hybrid Botulinal Neurotoxin Synthesis using Homobifunctional Sulfhydryl Linkers.

a. Materials and Methods

Bacterial cultures and neurotoxin purification. Type A and B botulinal neurotoxins were produced according to the methods described above.

Neurotoxin modification and thiol quantitation. Purified type A and B neurotoxins were modified by treatment with iodoacetamide (Sigma Chemical Co., St. Louis, Mo.) according to the method of Schiavo, et al. (1990) to block free sulfhydryls that interfere with subsequent biochemical reactions. Modification of type A neurotoxin prior to chain separation is illustrated in FIG. 2. Type B neurotoxin was modified in similar fashion. The degree of sulfhydryl modification was monitored by titration of free thiols using the method of Ellman (Arch. Biochem. Biophys. 82:70–77, 1959) as modified by Schiavo, et al. (1990).

Type A and B neurotoxin chain purifications. The motor neuron targeting and internalizing heavy chain of modified neurotoxins were separated from the catalytic light chains by two chromatographic steps (type A shown in FIG. 3). The heavy chains of type A and B neurotoxin were purified by the method of Sathyamoorthy and DasGupta (J Biol. Chem. 260:10461–10466, 1985). Specific toxicities of heavy chain preparations were between 10 and 100 i.p. $LD_{50}$/mg and were judged to be >95% homogeneous. Type A and B light chains from the same chain separations were judged to be >95% homogeneous on SDS-PAGE and had residual toxicities of 100–500 i.p. $LD_{50}$/mg protein.

Homobifunctional linkers. The two homobifunctional linkers used in the construction of the hybrid toxins in this work, bismaleimidohexane (BMH, FIG. 4), and 1,4-di[3'-(2'-pyridyidithio)-propionamido)'butane] (DPDPB, FIG. 4), were purchased from Pierce Biochemical, Rockford, Ill. BMH forms a non-reducible linkage between two thiol groups while DPDPB forms two reducible linkages between different thiols.

Electrophoresis and immunoblotting. Protein samples were examined electrophoretically using the Pharmacia Phastsystem (Pharmacia LKB Inc., Piscataway, N.J.) according to the manufacturers instructions. Precast 12.5% acrylamide and 10–15% gradient acrylamide gels (Pharmacia) were stained with 0.1% coomassie brilliant blue R250 in 16.7% acetic acid, 41.7% methanol. Gels were destained in 7.5% acetic acid, 25% methanol. Samples for electrophoresis were solubilized in 50 mM Tris-HCl, 5 M urea, 5% SDS, 20% glycerol, pH 6.8. Some samples were reduced by addition of dithiothreitol to a final concentration of 0.5%. All samples for SDS-PAGE were boiled for >5 minutes prior to electrophoresis. Protein bands from SDS-PAGE gels for analysis via immunoblotting were transferred to PVDF membranes using the Pharmacia semi-dry electrotransfer system according to the manufacturer's instructions. Serotype-specific polyclonal antibodies used for detection of type A and B botulinal toxins and separated chains were produced in rabbits at the Food Research Institute and were conjugated to alkaline phosphatase. The antibodies did not cross react between type A neurotoxin and separated chains and type B neurotoxin and separated chains. Alkaline phosphatase was detected using Sigma Fast nitro blue tetrazolium/bromo-chloro-indole phosphate tablets according to the manufacturers instructions (Sigma).

Toxin assays. Toxin titers were estimated in mice using the intraperitoneal method of Schantz and Kautter, J. Assoc. Off. Anal. Chem. 61:96–99, 1978 in 18–22 g, female, ICR strain mice.

Hybrid toxin construction and purification. Separated type A botulinal heavy chain (7.5 mg) and type B light chains (2.5 mg) were combined in a final volume of 20 ml and dialyzed in the case of the linker BMH against 20 mM sodium phosphate, 150 mM sodium chloride, 5 mM EDTA, 1 M urea, pH 7.0. The conjugation buffer for the linker DPDPB was 100 mM sodium phosphate, 5 mM EDTA, 1 M urea, 6.0. In both cases, the reaction mixtures were dialyzed against their respective buffers at 4° C. After three changes of dialysis buffer over a period of seven hours at 4° C., linkers dissolved in DMSO (10 mg/ml) were added at a final concentration of 1 mM linker. Linkage reactions were carried out in the dark at 4° C. for 16 hours (FIG. 5. Type A heavy chain conjugated to type B light chain via DPDPB.) Unreacted linker was removed by size exclusion chromatography on Sephadex PD10 columns.

b. Results

Toxicity and western blotting results. Toxicities of the various reagent components as well as final conjugates are shown in Table 3.

TABLE 3

Toxicities of hybrid toxins*

| Linker reaction | Type A botulinal heavy chain | Type B light chain | Toxicity (unreduced) | Toxicity (reduced) |
|---|---|---|---|---|
| BMH | 10–100 | 100–500 | ca. 1,000 | ca. 1,000 |
| DPDPB | 10–100 | 100–500 | >$10^6$ | ca. 500 |

*toxicities are expressed as mouse intraperitoneal $LD_{50}$/mg of protein.

Final yields for the above reactions were estimated to be 1 mg of DPDPB hybrid (10% theoretical yield) and BMH hybrid each.

Western blots of type A heavy chain and type B light chain hybrids separated on unreduced SDS-PAGE showed that hybrids (molecular weight approximately 155 kD) were reactive to both type A and B botulinum toxin specific antibodies. A faint band at ca. 200 kD representing two molecules of heavy chain was noted that was reactive to anti-type A antibodies. This band was estimated to represent <10% of the total amount of reactive protein per sample. In the case of DPDPB, this band disappeared upon reduction with dithiothreitol. Additional bands of 100 kD representing unreacted type A heavy chain and 55 kD representing type B light chain were estimated to represent approximately >50% of the starting material.

Samples of the DPDPB hybrid that had been reduced by the addition of 10 mM dithiothreitol prior to electrophoresis showed the disappearance of the 155 kD band. Samples of the BMH hybrid that had dithiothreitol added at the same level did not show any reduction in the reactivity of the 155 kD band indicating that the hybrid was resistant to reduction.

Genetic Engineering of Hybrid Toxins

1. In General

Because the genes encoding neurotoxin for all seven serotypes have been sequenced (reviewed in Minton, N. P., Curr. Top. Microbiol. Immunol. 195:161–194, 1995) it is possible to generate hybrid neurotoxins using genetic engineering techniques. This approach allows one to produce molecular gene fusions where two or more protein domains are linked by virtue of being encoded by a single piece of DNA. The structural chimeric gene is then inserted into an expression vector which contains regulatory elements such as control sequences for promoting and terminating RNA transcription, ribosome-binding sites and origin of plasmid replication. The recombinant plasmid can then be transformed into appropriate host cells for expression.

Using recombinant DNA technology, it is also possible to construct hybrid toxins containing not only the light chain from one *C. botulinum* serotype and the heavy chain from another, but also hybrid genes which contain the translocation domain of the heavy chain from one serotype, receptor binding domain of the heavy chain from another serotype, combined with the light chain of a third *C. botulinum* serotype. Thus, it is possible to construct a variety of new toxin molecules by combining any of the three functional domains from any *C. botulinum* neurotoxin serotypes.

In addition to the design and synthesis of entirely new polypeptides and proteins, genetic engineering methologies can also be applied to modify proteins with respect to their solubility, thermal and proteolytic stability, substrate specificity and affinity, and enzyme kinetics (reviewed in Offord, R. E., *Protein Engineering* 1:151–157, 1987; Leatherbarrow, R. J. and Fernst, A., *Protein Engineering* 1:7–16, 1986). For example, the light chain of neurotoxin is cleaved in vivo by mammalian proteases. Specific modifications can be introduced in these sites by site-directed mutagenesis at the DNA level, and then the protein expressed in the suitable host cells. Alteration of the protease-sensitive cleavage site(s) in the neurotoxin could greatly improve its stability and duration of action as a pharmaceutical agent.

Gene fusion technology for production of chimeric molecules may have certain advantages over chemical linkage: (1) a homogenous product is made; (2) there are no unreacted cross-linker groups; (3) unwanted protein sequences that may lead to nonspecific effects can be removed at the DNA level; and (4) large-scale production is possible in a suitable expression system.

The bacterial pathogen *Clostridium botulinum* is classified as a class 2 agent and biosafety level 2 (BL2) practices are recommended according to the U.S. Department of Health and Human Services (CDC, NIH, Biosafety in Microbiological and Biomedical Laboratories, 3 rd edition, 1993). Experiments involving the cloning and expression of *C. botulinum* neurotoxin require specific approval of Institutional Biosafety Committee before initiation of the experiments (Guidelines for research involving recombinant DNA molecules-NIH guidelines, 1995). Our laboratory has received approval for cloning and expression in *Escherichia coli* of individual chains and domains of *C. botulinum* neurotoxin under BL2 conditions. BoNT individual chains or domains are not toxic alone, thus, toxicity would only be regained in the presence of all three toxin domains (Smith, L. DS. and Sugiyama, H., *Botulism. The Organism, its Toxin, the Disease*, 2nd ed., (A. Barlows, ed.) Charles C. Thomas, Publisher, Springfield, Ill., 1988). Therefore, using heterologous hosts for production of individual neurotoxin domains is relatively safe, non-hazardous, and advantageous over the toxigenic *Clostridium botulinum* strains.

Several laboratories have cloned different clostridial neurotoxins genes or gene domains. *C. tetanus* neurotoxin (TeNT) receptor binding domain (~1.4 kbp) has been expressed in *E. coli* (Fairweather, N. F., et al., *J. Bacteriol.* 165:21–27, 1986; Fairweather, N. F., et al., *FEBS Lett.* 323:218–222, 1993; Makoff, A. J., et al., *Biotechnology* 7:1043–1046, 1989a; Figueiredo, D., et al., *Inf. Immun.* 63:3218–3221, 1995), *Saccharomyces cerevisiae* (Romanos, M. A., et al., *Nucl. Acids Res.* 19:1461–1467, 1991) *Pichia pastoris* (Clare, J. J., et al., *Biotechnology* 7:455–460, 1991) *Lactococcus lactis* (Wells, J. M., et al., *Mol. Microbiol.* 8:1156–1162, 1993) and a baculovirus system (Charles, I. G., et al., *Inf. Immun.* 59:1627–1632, 1991). BoNT/A receptor binding domain (~1.3 kbp) has been expressed in *E. coli* as well (Clayton, M. C., et al., *Inf. Immunol.* 63:2738–2742, 1995; Middlebrook, J. L. and Brown, J. E., *Curr. Top. Microbiol. Immun.* 195:89–122, 1995).

Available information on clostridial gene expression in *E. coli* and other heterologous hosts shows that this process occurs at low levels and is relatively inefficient (Minton, supra, 1995). A striking characteristic of clostridial DNA is its low G+C content, which ranges from about 20% to 38%. The G+C content of coding regions is consistently higher than that of non-coding intergenic regions. For example, the tetanus gene has a G+C content of 28% whereas that of the flanking non-coding regions is only 19% (Eisel, U., et al., *EMBO J.* 5:2496–2502, 1986).

The extremely low G+C ratio of clostridial DNA affects codon usage, which is strongly biased toward codons in which A and U predominate. A nearly identical pattern of codon utilization has been reported for different clostridial species. Biased codon usage is most prominent in amino acids with four to six synonymous codons. Among the six arginine codons, AGA predominates, whereas the CGX family is rarely used. Similarly, among six leucine codons, UUA is used preferentially. There is a strong prejudice toward use of A and U at the third position of all codons. Consequently, there are striking differences between clostridia and *E. coli* in codon utilization for the amino acids arginine, leucine, threonine, proline, glycine and isoleucine (Young M., et al., Genetics of Clostridium. In: *Biotechnology Handbook*, Clostridia (eds. N. P. Minton, D. J. Clarke) 3:63–103, 1989).

The available evidence suggests that clostridial genes are efficiently transcribed in *E. coli*. However, due to biased codons, translation of the clostridial mRNA in *E. coli* may be limited, such that the amount of the protein produced is very low or below the limits of detection. Makoff and coworkers (Makoff, A. J., et al., *Nucleic Acids Res.* 17:10191–10202, 1989b) have demonstrated that an unmodified gene fragment encoding only a subfragment of the heavy chain could be expressed in *E. coli* representing 3% to 4% of total cell soluble protein.

This low expression problem has been circumvented by either resynthesizing the gene to incorporate codons employed by highly expressed *E. coli* genes (Makoff, A. J., et al., supra, 1989a) or by using an expression host with a comparably low percentage G+C DNA content, such as *Lactococcus lactis* (Wells, J. M., et al., supra, 1993). These two strategies have resulted in levels of TeNT heavy chain fragment being attained which are equivalent to 14% and 22% of total cell protein, respectively. Similar strategies are now being employed to overexpress gene fragments of botulinal neurotoxins (BoNTs), primarily to assist in structure/function studies, but also for vaccination purposes (Clayton, M. C., et al., supra, 1995).

2. Expression of Individual Toxin Domains

Initially we attempted to express individual domains and subfragments of BoNT gene from *C. botulinum* type A (Hall strain) in *E. coli*. The pTrcHis (Invitrogen, San Diego, Calif.) *E. coli* expression system was chosen for the recombinant BoNT light chain purification. pTrcHis vectors are pUC-derived expression vectors that have been used for efficient protein expression and purification from cloned genes in *E. coli*.

High levels of expression of DNA sequences cloned into the pTrcHis vectors were made possible by the presence of the trc (trc-lac) promoter, and the rrnB antiterminator. The trc promoter contains the −35 region of the trp promoter together with the −10 region of the lac promoter. pTrcHis vectors also contain a copy of the lacl$^q$ gene which codes for the lac repressor protein. This allows for efficient repression of transcription of the cloned insert in *E. coli* regardless of whether the strain is lacl$_{q+}$ or lacl$^{q-}$. When expression is desired, *E. coli* are grown to mid-log phase and IPTG is added to 1 mM to induce expression via derepression. Translation was enhanced by the presence of a minicistron that provides highly efficient translation restart into the open reading frame (ORF) of the multiple cloning site.

present within the BoNT sequence, and additional bases to create in-frame fusion with the vector-borne open reading frame or stop codon. Each new restriction site is separated from the 5' end of the primer by at least 4 additional nucleotides to facilitate enzymatic digestion of the amplified DNA.

For example, primers A01 and A1321R (see Table 4) were used to amplify the entire light chain of BoNT/A (strain Hall). Primer A01 contains BoNT nucleotides 1–24 (shown in bold), unique recognition site for restriction endonuclease BamHl (underlined) to create in-frame fusion with the vector pTrcHis open reading frame, and 6 additional nucleotides (lower case letters) 5' to BamHl site to facilitate the restriction digestion. Primer A1321R contains BoNT nucleotides 1321–1344 (bold), followed by two stop codons (italics); Xbal restriction site (underlined), and 5 additional nucleotides (lower case letters) 5' to Xbal site to facilitate the restriction digestion.

TABLE 4

```
A01     (5')  gagatgGGATCCATGCCATTTGTTAATAAACAATTT (3')  (SEQ ID NO:1)
A1321R  (5')  acgccTCTAGATTATCACTTATTGTATCCTTTATCTAATGA (3')  (SEQ ID NO:2)
```

DNA inserts were positioned downstream and in frame with a sequence that encodes an N-terminal fusion peptide. This sequence codes for (5' to 3' from the promoter) an ATG translation initiation codon, six histidine residues in series that function as a metal binding domain in the translated protein, the bacteriophage T7 gene 10 translation enhancer, and an enterokinase cleavage recognition sequence.

The metal binding domain of the fusion peptide allowed simple, one-step purification of recombinant proteins by immobilized metal affinity chromatography. The enterokinase cleavage recognition site in the fusion peptide between the metal binding domain and the recombinant protein allowed for subsequent removal of this N-terminal fusion peptide from the recombinant protein.

The chosen system has a very stringent expression requirement in that there is little or no transcription of the target gene in an uninduced state. Expression of the protein is induced only by addition of IPTG. This provides a safe and non-hazardous system for production of any domain or segment of the neurotoxin gene. As mentioned above, BoNT individual chains or domains are not toxic (Smith, L. DS. and Sugiyama, H., supra, 1988). Thus, =toxicity of the toxin would be regained only in the presence of all toxin domains.

3. Cloning of Subfragments of the Toxin Gene

The subfragments of the BoNT/A gene encoding the entire light chain (nucleotides 1–1344), the entire heavy chain (nucleotides 1345–3891), channel forming (nucleotides 1345–2687) and receptor binding (nucleotides 2581–3891) domains or their truncated fragments (nucleotides 1345–1789; 1345–2083; 1345–2416; 3301–3891) of the heavy chain were cloned. This was accomplished via the polymerase chain reaction using specific oligonucleotides and *C. botulinum* chromosomal DNA as a template.

Each primer contained at least 20 nucleotides homologous to the target sequence and additional nonhomologous bases at their 5' ends. These extra nonhomologous nucleotides within the PCR primer contained a unique restriction site not Amplified DNA fragments were subcloned into the plasmid vectors-pBlueScript KS II. DNA sequences were verified by sequencing. The cloned gene fragments were inserted into *E. coli* expression vectors pTrcHis and gene expression analyzed. Bacterial cultures carrying expression constructs for the light chain and truncated heavy chain fragments contained inclusion bodies and the protein bands, corresponding in size to those expected, were revealed on Western blots.

4. Use of the Homobifunctional Linker Dithio-bis-maleimidoethane (DTME) in the Synthesis of Type E light Chain+Type A Heavy Chain Hybrid Botulinum Neurotoxin.

We have determined that the homobifunctional linker DTME (FIG. 6) is at least as reactive with free sulfhydryl groups present on separated chains of heterologous serotypes of botulinum neurotoxin as other previously described homobifunctional linkers.

Figure 6:
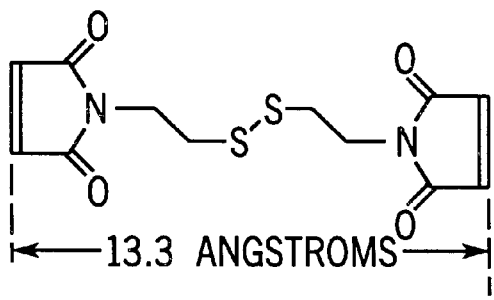
FIG. 6 is the structure of the sulfhydryl reactive homobifunctional linker dithio-bis-maleimidoethane (DTME).

FIG. 6 is the structure of the sulfhydryl reactive homobifunctional linker dithio-bis-maleimidoethane (DTME), with molecular weight 312.37 and spacer length 13.3 angstroms.

Figure 7:
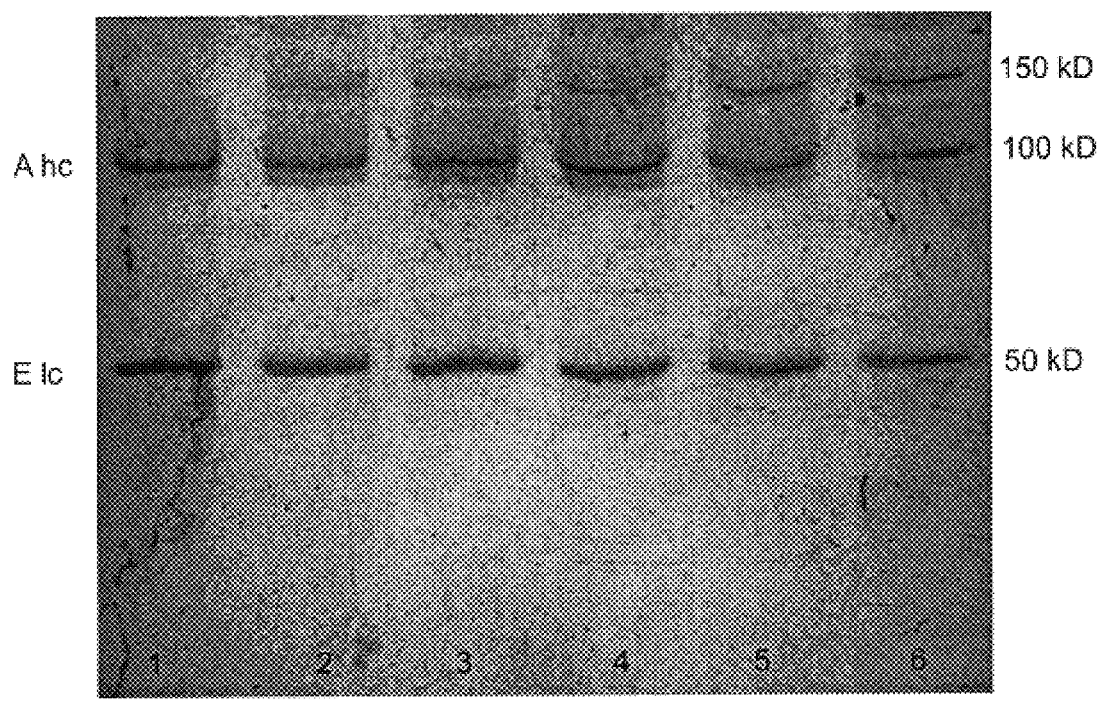
FIG. 7 is a copy of an SDS-PAGE showing the reaction of type A heavy chain and type E light chain using two different concentrations of the linker DTME over time.

FIG. 7 is a copy of an SDS-PAGE showing the reaction of type A heavy chain and type E light chain using two different concentrations of the linker DTME over time. Lane 1 represents the starting reagents, and lane 2 the reaction at 5 minutes. The appearance of high molecular weight species (>100 kD) indicates that the two heterologous chains are being combined. Lanes three and four show the same reaction at 15 minutes and 30 minutes respectively. The band corresponding to the hybrid toxin at 150 kD becomes more evident as the reaction proceeds. Lanes 5 and 6 represent a parallel reaction using twice the DTME concentration as the reaction shown in Lanes 2–4. The 150 kD hybrid toxin band is more evident in these lanes. Additionally, the disappearance of the starting reagents further supports the fact that the 150 kD band is composed of the type A heavy chain and type E light chain.

We claim:

1. A hybrid botulinal neurotoxin comprising:

(a) a botulinal neurotoxin light chain; and
(b) a botulinal neurotoxin heavy chain, wherein the light chain and heavy chain are not of the same serotype and wherein the light and heavy chains are linked by a reducible, disulfide homobifunctional linker and wherein the specific toxicity of the neurotoxin is it least $10^6$ $LD_{50}$/mg protein in vivo.

2. The neurotoxin of claim 1 wherein the heavy chain or light chain is isolated from a native botulinal neurotoxin molecule.

3. The neurotoxin of claim 1 wherein the heavy chain or light chain is obtained from a recombinant gene construct.

4. The neurotoxin of claim 1 wherein the entire hybrid neurotoxin is obtained from a recombinant gene construct.

5. A pharmaceutical composition comprising the neurotoxin of claim 1.

* * * * *

UNITED STATES PATENT AND TRADEMARK OFFICE
CERTIFICATE OF CORRECTION

PATENT NO.     : 6,444,209 B1
DATED          : September 3, 2002
INVENTOR(S)    : Eric A. Johnson et al.

It is certified that error appears in the above-identified patent and that said Letters Patent is hereby corrected as shown below:

<u>Column 1,</u>
Line 11, under STATEMENT REGARDING FEDERALLY SPONSORED RESEARCH AND DEVELOPMENT please add:

-- This invention was made with United States Government support awarded by the following agencies: DOD, DAMD17-92-M-6264. The United States has certain rights in this invention. --

Signed and Sealed this

Fourth Day of March, 2003

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 36
<212> TYPE: DNA
<213> ORGANISM: Clostridium botulinum

<400> SEQUENCE: 1
gagatgggat ccatgccatt tgttaataaa caattt                     36

<210> SEQ ID NO 2
<211> LENGTH: 41
<212> TYPE: DNA
<213> ORGANISM: Clostridium botulinum

<400> SEQUENCE: 2
acgcctctag attatcactt attgtatcct ttatctaatg a               41